US010551360B2

(12) United States Patent
Nielsen et al.

(10) Patent No.: US 10,551,360 B2
(45) Date of Patent: Feb. 4, 2020

(54) LOW DEAD-VOLUME CONNECTOR FOR FLUID CHROMATOGRAPHY

(71) Applicant: Bruker Daltonik GmbH, Bremen (DE)

(72) Inventors: Peter A. Nielsen, Marslev (DK);
Nicolai Bache, Odense S (DK);
Christoph Gebhardt, Bremen (DE);
Ralph Kikillus, Bremen (DE)

(*) Notice: Subject to any disclaimer, the term of this patent is extended or adjusted under 35 U.S.C. 154(b) by 343 days.

(21) Appl. No.: 15/290,170

(22) Filed: Oct. 11, 2016

(65) Prior Publication Data

US 2018/0100837 A1    Apr. 12, 2018

(51) Int. Cl.
*G01N 30/60* (2006.01)
*F16L 19/02* (2006.01)

(52) U.S. Cl.
CPC ...... *G01N 30/6034* (2013.01); *F16L 19/0206* (2013.01); *G01N 30/6026* (2013.01); *G01N 30/6039* (2013.01)

(58) Field of Classification Search
CPC ........... G01N 30/6026; G01N 30/6034; G01N 30/6039; F16L 19/0206; F16L 19/0212

USPC ............... 285/246, 342; 210/198.2
See application file for complete search history.

(56) References Cited

U.S. PATENT DOCUMENTS

| | | | | |
|---|---|---|---|---|
| 4,083,702 | A | * | 4/1978 | Hartigan ............ G01N 30/6039 |
| 4,690,437 | A | | 9/1987 | Anderson, Jr. |
| 4,792,396 | A | * | 12/1988 | Gundelfinger ............. 210/198.2 |
| 2012/0061955 | A1 | * | 3/2012 | Hochgraeber ..... G01N 30/6026 285/342 |
| 2014/0131997 | A1 | * | 5/2014 | Burger ............... G01N 30/6039 |
| 2015/0300542 | A1 | | 10/2015 | Graham et al. |
| 2016/0116088 | A1 | | 4/2016 | Graham et al. |

FOREIGN PATENT DOCUMENTS

GB   2553169 A   2/2018

* cited by examiner

*Primary Examiner* — Zachary T Dragicevich
(74) *Attorney, Agent, or Firm* — Benoit & Côté Inc.

(57) ABSTRACT

A low dead-volume connector for fluid chromatography, such as liquid chromatography and gas chromatography, has a female assembly including a receiving member being designed and configured to receive, and releasably interlock with, a male assembly. The connector is particularly suited for high performance liquid chromatography (HPLC) applications.

20 Claims, 5 Drawing Sheets

Disassembled state
(male and female assemblies)

Disassembled state
(male and female assemblies)

Assembled state
(male assembly)

LOW DEAD-VOLUME CONNECTOR FOR FLUID CHROMATOGRAPHY

BACKGROUND OF THE INVENTION

Field of the Invention

The invention relates generally to connectors for fluid chromatography, such as liquid chromatography (LC) and gas chromatography (GC), particularly for the high performance regime, such as high pressure liquid chromatography—HPLC.

Description of the Related Art

Various design solutions for fluid connectors in general exist in the state of the art, a selection thereof being summarized in the following.

The U.S. Pat. No. 4,690,437 A to Anderson describes a fitting connecting a tubing end to a fluid conducting member which has a fluid port and end walls surrounding the port. The fitting comprises a ferrule of resilient deformable material having a forward portion with a wide flat sealing surface which is adapted to mate with and sealingly engage the end wall surrounding the port.

The U.S. Pat. No. 5,298,225 A to Higdon discloses a detachable column cartridge for a gas chromatograph. The cartridge column contains analytical and reference columns, a heater and a thermocouple, and connects via detachable connectors to a base unit containing an injector, a detector and other components normally found in gas chromatographs. The cartridge arrangement is stated to permit a substitute column to be connected to the base unit easily, in the field, when different gases are to be separated and analyzed.

The international application WO 97/45666 A1 illustrates a fitting assembly that comprises an insert.

The U.S. Pat. No. 6,273,478 B1 to Benett et al. discloses a miniature connector for transmitting microliter quantities.

The U.S. Pat. No. 6,575,501 B1 to Loy Jr. et al. shows a deformable bushing to seal tubing to a receiving body.

The U.S. Pat. No. 9,091,693 B2 to Hochgraeber et al. presents a plug unit for connecting a capillary tube to a bushing unit, the plug unit being characterized particularly through the rigid connection between a pressure piece, an annular sealing element and a plug capillary tube that is brought about in particular by cramping.

The European patent 1 457 775 B1 discloses a plastic hose with a tubular wall from polyether ether ketone (PEEK), polyaryletherketone (PAEK), or polyether ether ketone ketone (PEEKK) and with a connector head for connecting the plastic hose to a connector head of a hose end, tube-end or similar device, wherein the connector head comprises an expansion of the wall of the plastic hose and the expansion consists likewise of PEEK, PAEK, or PEEKK, and further wherein the expansion is molded onto the outside of the wall.

In view of the above, there is still a need for improvement with connectors for fluid chromatography, such as liquid chromatography and gas chromatography. Objectives and achievements of the invention will readily suggest themselves to those of skill in the art upon reading the following disclosure.

SUMMARY OF THE INVENTION

The invention relates generally to a connector for fluid chromatography, capable of achieving low or even zero dead-volume connection. The connector has a female assembly with a receiving member being designed and configured to receive, and releasably interlock with, a male assembly. The male assembly comprises a capillary conduit for transmitting chromatography fluid (mobile phase), such as liquid or gas, a sealing gasket accommodating a front end portion of the capillary conduit and having a front end flange with a beveled rearward facing surface, a force-transmitting member slidably accommodating a portion of the sealing gasket and having a rearward facing force-receiving surface as well as a beveled front face, the dimensions of which are substantially complementary to those of the beveled rearward facing surface of the front end flange for exerting axial and radial pressurization thereon, and a hollow handling nut comprising a passage in which a (distal) portion of the capillary conduit is (floatingly) accommodated and having a forward facing force-exerting surface being configured to contact the rearward facing force-receiving surface for transmitting axial forces there-between.

The beveled front face of the force-transmitting member being directly pressed against the beveled rearward facing surface at the front end flange of the sealing gasket, upon engaging the male assembly with the female assembly, and without the aid of any additional force conveying means, has the benefit that the resultant axial and radial forces, being introduced to the front end region of the male assembly (solely) via the force-transmitting member and employed for generating the seal, are exerted in a very homogeneous manner about the circumference of the capillary conduit which strengthens and generally improves the sealing effect.

In order to slidably (or floatingly) accommodate a certain element, such as the sealing gasket, within another element, such as the force-transmitting member, a slight undersize of the engaging element in relation to the receiving element may be used. The magnitude of such undersize can be in the range of several hundred micrometers, such as 300 micrometers, for instance. In particular embodiments, slidable accommodation or floating engagement can mean that the two elements, being engaged within one another or the one accommodating the other, should fall apart when turned from the horizontal to the vertical.

Preferred applications for such designs include nanoflow HPLC, using flow rates between about 1 to 1000 nanoliters per minute, and high flow HPLC, using flow rates of about one microliter per minute and above. Operating pressures may range from 5 to 300 bar and above, as may correlate to ultra performance LC (UPLC) and ultra high performance LC (UHPLC) where typical pressures can be in the range up to or even above 1200 bar.

In various embodiments, the beveled rearward facing surface and the beveled front face can be configured and dimensioned such as to be in substantially full face contact when the male and female assemblies are engaged with one another. In so doing, pressurization of the sealing gasket can be spread over a comparatively large area, thereby reducing highly localized wear and tear by the repeated disengaging and re-engaging of the male and female assemblies during the lifetime of the connector.

In various embodiments, a preferred range for angles of the beveled rearward facing surface (and preferably also the complementary beveled front face of the force-transmitting member) in relation to a longitudinal axis of the male assembly is between 30° and 70°, such as 45° or 60°. Regarding the full three-dimensional embodiment of the sealing gasket, the beveled rearward facing surface at the front end flange corresponds to an outer frusto-conical surface of certain inclination in relation to the central axis. It goes without saying that the division of axial forces into axial and radial sub-forces at the front end flange correlates with the angle of inclination; the steeper the angle in relation to the axis, the less portions of the initial axial force will be deflected to the radial inward direction.

In various embodiments, a shape of at least one of the capillary conduit, sealing gasket, and force-transmitting member is preferably substantially annular cylindrical, generally improving the ease-of-production of these elements of the male assembly. The force-transmitting member's inner diameter can be in the lower millimeter range, such as between 0.5 and two millimeters, for example, whereas its outer diameter could be about double that. It goes without saying that the dimensions of the capillary conduit and sealing gasket are readily adaptable to such dimensions. Exemplary values for the typical extensions along the longitudinal axis for the individual elements would be about four millimeters for the sealing gasket, thirteen millimeters for the force-transmitting member and twenty millimeters or even more for the hollow handling nut.

In various embodiments, the sealing gasket may stand out slightly from the front end portion of the capillary conduit in a disengaged condition of the male and female assemblies, and becomes compressed into a substantially flush alignment with the front end portion of the capillary conduit when the male and female assemblies are engaged with one another. Alternatively, it is also possible to arrange already for a flush alignment in the disengaged condition of the male and female assemblies.

In various embodiments, an outer diameter of the force-transmitting member may substantially match that of the front end flange in order to facilitate neat and stable fitting of the male assembly in the receiving member of the female assembly without leaving much unoccupied volume.

In various embodiments, the receiving member can be one of a one-sided port and a double-sided union. In case of the one-sided port variant, it may have a doubly stepped circular recess, the inner diameter of the first recess step being adapted to the outer diameter of one of the front end flange and the force-transmitting member, and the inner diameter of the second recess step being larger than that of the first recess step. In case of the double-sided union variant, the aforementioned design features could just be mirrored and reproduced in an abutting (and opposing) relation as will become apparent from embodiments to be described further below.

In certain embodiments, a transition between the second recess step and the first recess step preferably has conical shape, though it is also conceivable to design it with a perpendicular edge relative to the axis of the connector, for instance.

In some embodiments, both the second recess step and a first section of the hollow handling nut can have complementary interlocking mechanisms, an example of which would comprise an external thread foreseen at an outer circumferential surface of the first section of the hollow handling nut and a complementary internal thread foreseen at an inner circumferential surface of the second recess step. Other interlocking mechanisms are likewise conceivable, such as a bayonet fitting, for instance, and will be implemented by a skilled practitioner as is deemed fit.

In various embodiments, the one-sided port may have an axial through-bore located such that it comes to rest in opposing relation to the front end portion of the capillary conduit when the male and female assemblies are engaged with one another, thereby facilitating for largely uninterrupted continuation of a fluid conduit within the receiving member.

In various embodiments, the axial through-bore of the one-sided port can accommodate tubing that functions as a continuation of the capillary conduit when the male and female assemblies are engaged with one another. In the simplest example, the tubing is of the same design and configuration as the capillary conduit, such as consisting of a fused silica capillary, in order to render a good geometric match of the two abutting front ends.

In various embodiments, the one-sided port may have a substantially flat bottom against which a front end of the male assembly is pressed when the male and female assemblies are engaged with one another. Such design ensures that the sealing is effected in the plane of the interface between the capillary conduit and any downstream tubing being coupled thereto. The main advantage of such bottom seal over other designs, such as a ferrule seal, is basically the low or even zero dead-volume.

In various embodiments, the sealing gasket may be jointed radially inward to the capillary conduit via opposing inward-facing and outward-facing surfaces, respectively. Preferably, the joint is produced by one of adhesive, radial swaging, radial plastic deformation, and heat welding or any combination of these techniques. A skilled practitioner will understand that the heat necessary for welding can be generated by a plurality of means, such as infrared radiation. The joint serves to render the capillary conduit and sealing gasket thusly jointed unmovable relative to one another even when exposed to external strain, such as pressurization of the backward facing shoulder at the sealing gasket's front end flange by the beveled front end of the force-transmitting member, for example.

In some embodiments, a glue joint can be established spaced apart from the front end portion of the capillary conduit. In so doing, any potential issues with particulate matter and outgassing from the glue coming in contact with the fluid-conveying inner bore of the capillary conduit and contamination of the fluid (mobile phase) can be avoided to a large degree or even completely eliminated. Spaced apart may be understood as a distance away from the front end portion of the capillary conduit that corresponds at least to the longitudinal extension of the front end flange of the sealing gasket which may amount to several millimeters. Some embodiments of the sealing gasket may feature an inner, circumferential recess for receiving the set glue upon jointing.

The hollow handling nut preferably comprises a first section with an interlocking mechanism designed and configured to cooperate with a complementary interlocking mechanism foreseen at the receiving member, such as the one-sided port or double-sided union, and further preferably comprises a second section for manual or tool-assisted tightening the male assembly in the female assembly. A practitioner will understand that the second section can be equipped with a polygonal feature, such as a pentagonal feature, at an outer circumference in order to facilitate mounting a correspondingly adapted wrench thereon (for tool-assisted tightening). A polygonal feature ensures, for instance, that standard wrenches are not applicable, but only special tools which can ensure that the whole fitting is not overtightened. In preferred embodiments, the complementary interlocking mechanisms can comprise external and internal threads.

In various embodiments, the first section may comprise a cylindrical cavity in which a (distal) portion of the force-transmitting member is slidably (and rotatably) accommodated. The forward facing force-exerting surface at the hollow handling nut may be a flat ground in the cylindrical cavity which, upon putting together the male assembly, preferably contacts a flat (or unbeveled) back face of the force-transmitting member as an embodiment of the rearward facing force-receiving surface.

In various embodiments, the capillary conduit might have an outer protective sleeve (or outer coating layer or additional protective tubing) at a position spaced apart from its front end portion (at a distal portion), the sleeve (or coating layer or protective tubing) being designed and configured to protect the capillary conduit from mechanical and other (external) stresses.

BRIEF DESCRIPTION OF THE DRAWINGS

The invention can be better understood by referring to the following figures. The elements in the figures are not necessarily to scale, emphasis instead being placed upon illustrating the principles of the invention (often schematically). In the figures, corresponding parts are generally designated by identical last two digits of the reference numerals throughout the different views.

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Fluid connectors are designed and configured to establish a fluid communication between an upstream device and a downstream device via intermediate fluid conduits. The upstream device may be a liquid or gas chromatograph, or more specifically the associated chromatographic column, which outputs an eluent of substances that have been separated chromatographically. The downstream device may be a mass spectrometer, or more specifically the ion source thereof, such as an electrospray ion source or electron ionization source. Those of skill in the art are familiar with such kind of instrumentation so that there is no need to elaborate thereon in further detail here. It is to be understood that a chromatography fluid will comprise a mobile phase, in the case of liquid chromatography usually made up of a suitable solvent, into which the sample to be analyzed has been spiked at a point upstream of the chromatographic column.

Figure 1A:
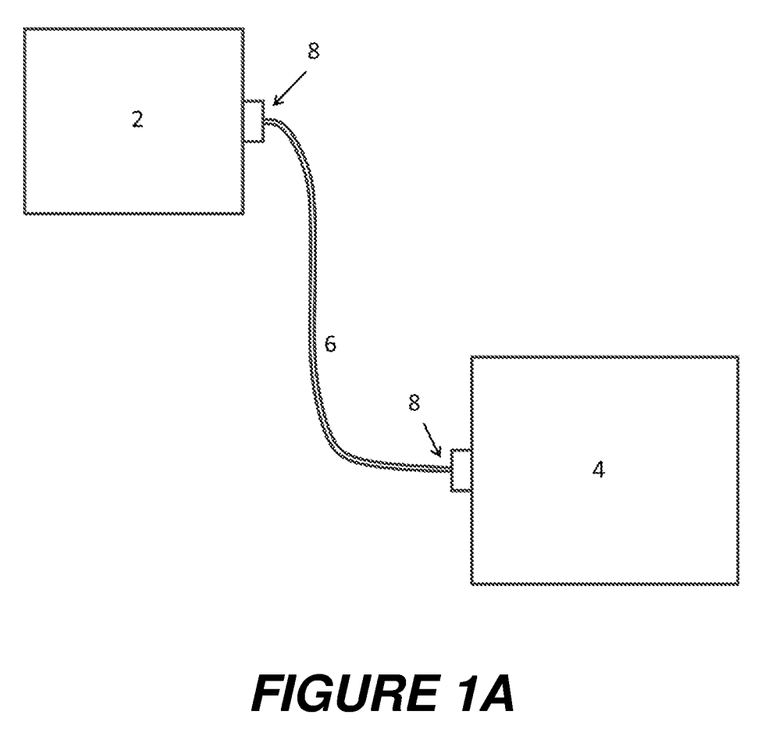
FIGS. 1A and 1B illustrate schematically a fluid connection between an upstream device, such as a liquid or gas chromatograph, and a downstream device, such as an ion source of a mass spectrometer.

FIG. 1A schematically shows by way of example an upstream device 2, such as a liquid or gas chromatograph, and a downstream device 4, such as a mass spectrometer, which are both fluidly connected to one another by means of a conduit 6. The conduit 6 may be flexible and coupled to the two devices 2, 4 by virtue of fluid connectors 8. Such connectors may be designed according to principles of the present invention to be expounded in the following.

Figure 1B:
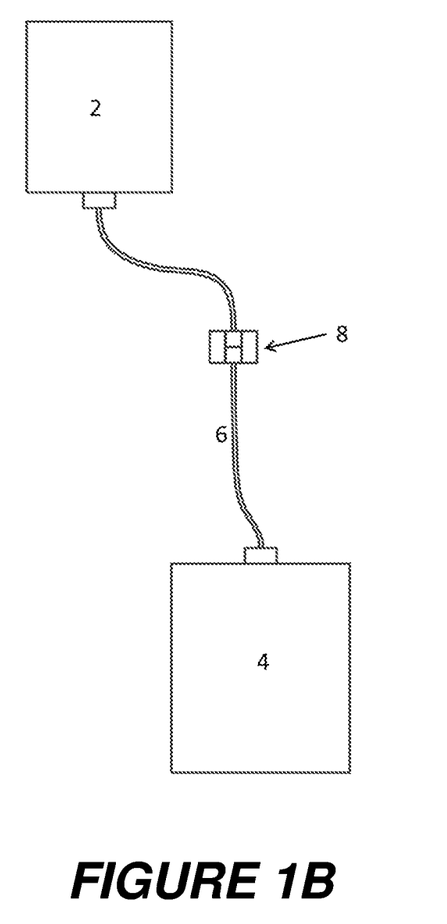

FIG. 1B illustrates a connector 8 of slightly different design where a receiving member of a union receives two male assemblies, such as to be described further below, at two sides facing away from one another.

Figure 2A:
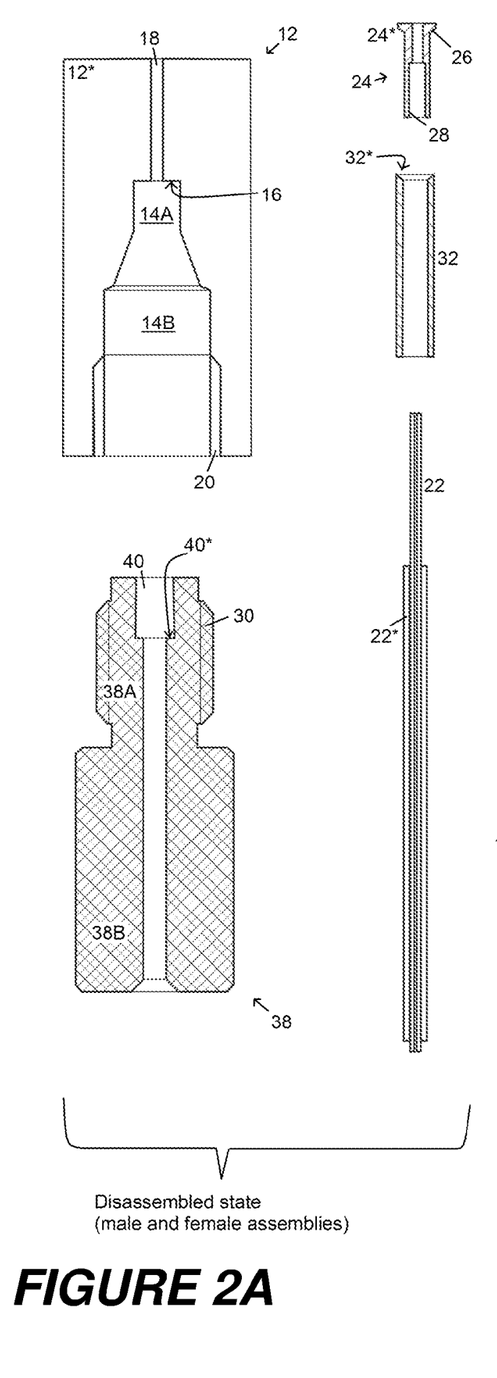
FIGS. 2A to 2C schematically show an embodiment of a connector according to principles of the invention.

FIG. 2A shows the different parts of a connector 8 in a disassembled view. The basic components are the male assembly 10 and the female assembly 12. The female assembly 12 comprises a one-sided port 12* that basically may consist of a block of (synthetic or metallic) material into which two circular recesses 14A, 14B have been worked. The first circular recess 14A has a flat bottom wall 16 including a through-bore 18 for accommodating a continuation fluid conduit (not shown here). The second circular recess 14B has an internal thread 20 that is designed and configured to mate with an external thread foreseen at the hollow handling nut of the male assembly 10 to be discussed further below so as to facilitate a releasable interlocking function between the male and female assemblies 10, 12. A transition between the first and second circular recesses 14A, 14B tapers conically in the embodiment shown. It will, however, be appreciated by a skilled practitioner that the transition might also be designed in a different manner, such as substantially rectangular, for instance.

The male assembly 10 is comprised basically of four different elements, and these will be referred to first in an isolated manner. At the core of the male assembly 10 is a capillary conduit 22, such as a capillary tube. An example of such conduit 22 would be a fused silica capillary, PEEKsil™ capillary or polyimide-clad fused silica capillary, a part of which is shown in FIG. 2A. Inner bore diameters may be in the range of several micrometers, such as ten up to twenty micrometers reaching up to several hundreds of micrometers depending on the intended field of application. Typical dimensions for the outer diameter can be 150 to 380 micrometers and lengths may be between a few centimeters up to a meter and even more. In a rearward (or distal) part, the capillary conduit 22 may have a particular coating layer or additional protective tubing or protective sleeve 22* in order to render it more robust toward external stresses, such as mechanical stresses.

A sealing gasket 24 of substantially cylindrical shape is provided to be arranged on, and glued (or otherwise attached) to the front end of the capillary conduit 22. The sealing gasket 24 may be made from any material that is generally deformable so that it is able, upon compression, to reliably seal two abutting surfaces, such as the flat bottom wall 16 of the first circular recess step in the one-sided port 12* and the front end of the male assembly 10. In preferred examples, the sealing gasket 24 is created in such a way as to prevent any material from coming into contact with the fluid stream in the bore of the capillary conduit 22 which would run the risk of contaminating any working fluid (mobile phase) therein. In the embodiment shown, the sealing gasket 24 has a flanged front end 24* which has a beveled rearward facing surface 26.

The front end flange 24* has a front plane that allows for a leak tight seal with the flat bottom wall 16 of the one-sided port 12* and also a backward shoulder 26 on to which force is applied, when the male and female assemblies 10, 12 are connected. In a preferred embodiment of the front end flange 24*, the backward shoulder 26 has a defined angle to the axis of the male assembly 10 of about 45° or 60°, by way of example. In this manner, the axial force applied to the sealing gasket 24 via the backward shoulder 26 at the front end flange 24* is split into an axial and radial sub-force. While the axial sub-force ensures the sealing in the one-sided port 12*, the radial inward sub-force ensures sealing around the capillary conduit 22. So doing may create a sealing zone additional to the glued zone (or generally attach zone) when the latter is spaced apart from the front face of the male assembly 10, such glued zone (or generally attach zone) mainly holding the capillary conduit 22 axially in place in order to take pressures up to 1000 bar without slipping. The additional sealing zone at the front end, when there is no glue joint at this point, also separates the area that may be affected by the fluid (mobile phase) in the capillary conduit 22 from the set glue, thus minimizing contamination issues due to leaked solvent or mobile phase or in turn outgassing and particulate shedding from the glue.

The capillary conduit 22 can be positioned within the sealing gasket 24 either flush or slightly retracted so that the front face of the sealing gasket 24 slightly protrudes from the front end portion of the capillary conduit 22. Those of skill in the art will acknowledge that the proposed front end flange 24\* actually allows a real flush position, generating a true zero dead-volume connection, because the force is applied only to and via the front end flange 24\* and not directly to the capillary conduit 22/sealing gasket 24 sub-assembly. Moreover, the angled rearward facing shoulder 26 at the front end flange 24\* makes the deformation of the sealing gasket 24 such that the capillary conduit 22 is stationary.

A lasting joint can be established between the capillary conduit 22 and the sealing gasket 24 by gluing them together via the radially outward and inward facing opposing circumferential surfaces, respectively. The sealing gasket 24 can be provided with a (optional) geometric feature which facilitates the gluing process, such as an internal, circumferential recess 28 for accommodating the set glue after the jointing, for instance. Other embodiments may employ heat welding where a part of the material at the radially opposing circumferential surfaces of the two elements to be jointed is exposed to electromagnetic radiation, such as infrared light, so that it becomes partially molten and establishes an adhesive bond between the two contacting opposing surfaces upon re-hardening. Other ways of creating a joint are heating the complete body (or bodies) or just the surface(s) to be jointed and then fusing them together with the corresponding counterpart by molding, laser irradiation etc.

Further provided is a force-transmitting member 32 being implemented as a hollow cylinder here through which the capillary conduit 22 is bound to reach and made of any rigid and dimensionally stable material, such as stainless steel or hard plastic, for example. In the embodiment shown, the cylinder has an inner diameter dimensioned such as to closely but slidably accommodate a rearward portion of the sealing gasket 24. Thus, the force-transmitting member 32 is not fixed to either the sealing gasket 24 or the capillary conduit 22 but can slide freely along the axis of the male assembly 10. The free movability provides for the particular advantage of such design in that the front end flange 24\* of the sealing gasket 24 can be compressed against the flat bottom wall 16 of the one-sided port 12\*. During the process of engaging and interlocking the male and female assemblies 10, 12 with one another, the force-transmitting member 32 actually translates axially with respect to the capillary conduit 22, and, as it is also rotatable in respect of the capillary conduit 22 and sealing gasket 24 it surrounds, no torsional stress will be imparted on the front end flange 24\* of the sealing gasket 24 rendering such design especially benign as far as mechanical stresses during engaging and disengaging the male and female assemblies 10, 12 are concerned.

The force-transmitting member 32 may have a unique beveled front end 32\* which transfers the force to the beveled rearward facing surface 26 at the front end flange 24\* of the sealing gasket 24. The bevels of front end flange 24 and force-transmitting member 32 are preferably complementary to one another in order to establish the largest possible force-transmitting contact (full face contact), but do not have to be exactly the same actually. In fact, it might be beneficial for some embodiments (not shown) to deliberately mismatch them in order to influence the exact axial and radial force profiles. A lower angle of the force-transmitting member's 32 front face 32\* would branch off more force on the sealing gasket 24 in the radial direction on the expense of that in the axial direction. In further refined embodiments, also force-transmitting interfaces having multiply angled opposing surfaces (not illustrated here) could principally be envisaged.

Viewed from the outside, the hollow handling nut 38 has two distinct sections. The first section 38A has an outer diameter that is adapted to substantially match the inner diameter of the second recess step 14B of the one-sided port 12\*, and further comprises an external thread 30 which is configured to mate with the internal thread 20 foreseen at the second recess step 14B of the one-sided port 12\* such as to allow for releasable interlocking between the male and female assemblies 10, 12 of this embodiment. The first section 38A further comprises a cylindrical cavity 40, having a flat cavity ground 40\*, in which a rear portion of the force-transmitting member 32 is slidably (and rotatably) accommodated. The straight back face of the force-transmitting member 32 (as rearward facing force-receiving surface) may be bound to contact the cavity ground 40\* in the first section 38A of the hollow handling nut 38 (as forward facing force-exerting surface). It is at this interface that compression forces are transmitted from the hollow handling nut 38 via the force-transmitting member 32 to the front end (or sealing region) of the male assembly 10.

The second section 38B of the hollow handling nut 38 has a larger outer diameter and is designed and configured such as to be easily manually actuated, or operated with a wrench, so that it can serve as a manual or tool-assisted tightening section, respectively. For manual operation, the outer circumferential surface of this second section 38B may, for example, be textured in order to render a positive haptic feedback when being touched by an operator. For this purpose, an outer diameter of the second section 38B may be in the millimeter range, such as between six and seven millimeters, for example, but can generally be chosen by a skilled practitioner as is deemed fit.

For tool-assisted operation, the second section 38B may have a pentagonal feature (not shown) which allows mounting of an especially dimensionally adapted wrench in order to prevent involuntary tightening or loosening the connection. The hollow handling nut 38 generally serves to exert an axial force on the force-transmitting member 32 and, topologically, slidably accommodates the capillary conduit 22 in an internal passage so that the two may slide freely against one another along the axis. In particular embodiments, this axial motion can be limited by additional stops on the capillary conduit's protective coating or protective tube 22\* in order to keep the parts of the connector 8 from falling apart and to avoid potential damage if the individual parts of the connector 8 are exposed.

Figure 2B:
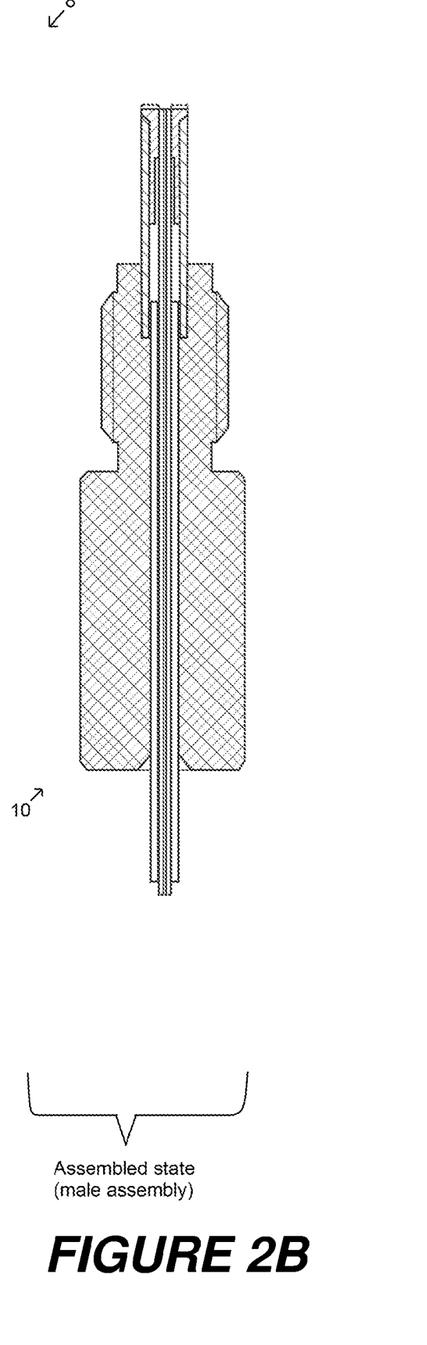

FIG. 2B (to the right of FIG. 2A) shows the male assembly 10 put together and ready for being inserted into the one-sided port 12\* of the female assembly 12. As can be seen, the front end flange 24\* of the sealing gasket 24 is arranged about flush with the front end of the capillary conduit 22 (solid contour) so that the front end flange 24\* will contact the flat bottom wall 16 in the one-sided port 12\* upon insertion of the male assembly 10 into the female assembly 12, thereby establishing the seal. A skilled practitioner will appreciate, however, that the sealing gasket 24 could be designed and arranged on the capillary conduit 22 such that its front end flange 24* extends longitudinally slightly beyond the front end of the former (dashed contour). Upon insertion into the receiving member 12, the front end flange 24 would then start to be deformed as soon as its forward surface contacted the flat bottom wall 16 until a substantially flush alignment (and compressed condition of the front end flange 24*) is achieved.

Figure 2C:
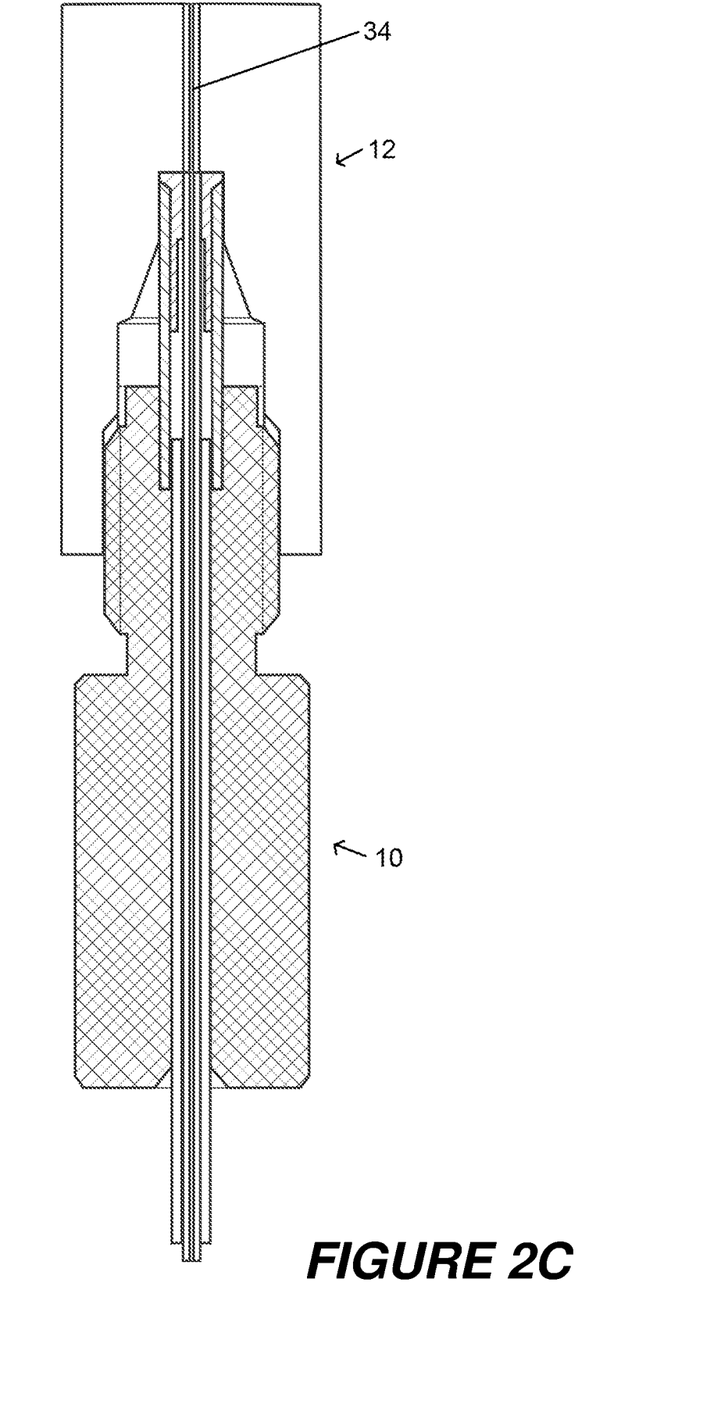

FIG. 2C shows the connection between the male and female assemblies 10, 12 of FIGS. 2A and 2B when the internal and external threads 20, 30 of the second recess step 14B in the one-sided port 12* and the first section 38A of the hollow handling nut 38 have been engaged with one another. The flat ground 40* in the hollow cylindrical recess 40 of the first section 38A of the hollow handling nut 38 contacts the flat back face of the force-transmitting member 32, thereby transmitting axial as well as (by virtue of the beveled interface) radial compressing forces directly on the front end flange 24* at the sealing gasket 24 engaging with the flat bottom wall 16 of the first recess step 14A in the one-sided port 12*. The forces are split into an axial part that drives the front end flange 24* together with the capillary conduit 22 against the flat bottom wall 16* and a radial part that ensures the tight engagement of the sealing gasket's front end flange 24* with the accommodated front face of the capillary conduit 22. In this manner, the interface is sealed such that no fluid (mobile phase) can escape the inner bore of the capillary conduit 22 radially but will rather flow forward into the adjacent connection tubing 34 foreseen in the through-bore 18 of the one-sided port 12*. This design renders the pressurization forces being exerted very homogeneously axially as well as radially about the circumference of the sealing gasket 24 and thereby allows for a very tight and reliable seal, suited for high pressure liquid chromatography applications often operating in a pressure range from about 50 to 350 bar or even higher up to 1200 bar, essentially without any significant dead-volume at the interface that could degrade performance, such as by sample carry-over or tailing.

A skilled practitioner will appreciate that one beneficial effect, among others, of the dimensionally stable force-transmitting member 32 surrounding the deformable sealing gasket 24 and comparatively delicate capillary conduit 22 is to prevent pressurization forces exerted on the sealing gasket 24 from being partially dissipated in radial outward directions which would weaken the pressure seal in the axially forward direction at the front end of the male assembly 10.

Figure 3:
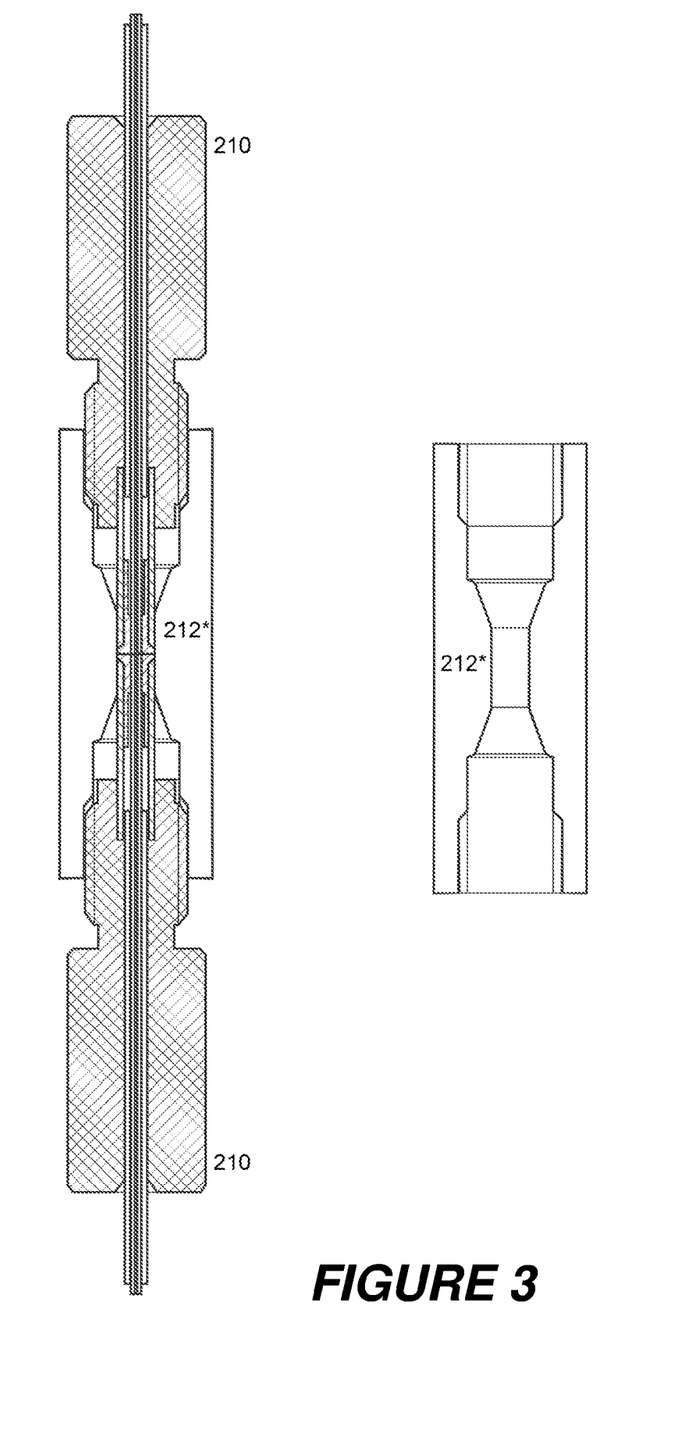
FIG. 3 shows a connector according to principles of the invention having a female assembly with receiving member that takes the shape of a double-sided union.

The example implementation from FIGS. 2A to 2C referred to above shows a one-sided port 12* to which a male assembly 10 is coupled on only one side thereof, correlating somehow to the depiction in FIG. 1A. Departing from this one-sided approach and rather correlating to the sketch in FIG. 1B, FIG. 3 illustrates schematically a female assembly that comprises a receiving member which is accessible to male assemblies 210 at two (opposing) sides thereof, forming a double-sided union 212*. In other words, the capillary conduit of one of the male assemblies 210 abuts the respective other one and thereby represents the continuation conduit of the respective other male assembly 210 in this example and vice versa. In the embodiment shown, the double-sided union has a symmetric design in that both recesses have the same size and geometry. A skilled practitioner will understand however that asymmetric designs are likewise conceivable, such as recesses configured for receiving male assemblies of different dimensions or configuration.

In the example of FIG. 3, however, the two male assemblies 210 have the same exemplary design as that shown in FIG. 2B, though a skilled practitioner will understand that this embodiment is not to be understood restrictively. Favorably, the axial extension of the two internal threads at the respective second recess steps are dimensioned such that, when the male assemblies 210 have been screwed into the receiving member to the maximum, the respective front ends come to lie at about the center of the union piece 212* as shown, thereby ensuring reliable radial guidance during the insertion.

In the above-explained embodiments, a pair of mating threads is used to deliver the releasable interlocking function between the male and female assemblies. A skilled practitioner will understand, however, that this function can be achieved in many other suitable ways, such as by a bayonet fitting, for example.

The invention has been shown and described with reference to a number of different embodiments thereof. It will be understood, however, that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims.

The invention claimed is:

1. A connector for fluid chromatography having a female assembly including a receiving member being designed and configured to receive, and releasably interlock with, a male assembly, the male assembly comprising:
   a capillary conduit for transmitting chromatography fluid;
   a sealing gasket accommodating a front end portion of the capillary conduit and having a front end flange with a beveled rearward facing surface;
   a force-transmitting member slidably accommodating a portion of the sealing gasket using a slight undersize of the sealing gasket in relation to the force-transmitting member such that the sealing gasket and the force-transmitting member, the latter accommodating the former, fall apart when turned from a horizontal alignment to a vertical alignment, and having a rearward facing force-receiving surface as well as a beveled front face, the dimensions of which are substantially complementary to those of the beveled rearward facing surface of the front end flange for exerting axial and radial pressurization thereon; and
   a hollow handling nut comprising a passage in which a portion of the capillary conduit is accommodated and having a forward facing force-exerting surface being configured to contact the rearward facing force-receiving surface for transmitting axial forces there-between.

2. The connector of claim 1, wherein the beveled rearward facing surface and the beveled front face are configured and dimensioned such as to be in substantially full face contact when the male and female assemblies are engaged with one another.

3. The connector of claim 1, wherein an angle of the beveled rearward facing surface in relation to a longitudinal axis of the male assembly is between 30° and 70°.

4. The connector of claim 3, wherein the angle is 45° or 60°.

5. The connector of claim 1, wherein a shape of at least one of the capillary conduit, sealing gasket, and force-transmitting member is substantially annular cylindrical.

6. The connector of claim 1, wherein an outer diameter of the force-transmitting member substantially matches that of the front end flange.

7. The connector of claim 1, wherein the receiving member is one of a one-sided port and a double-sided union.

8. The connector of claim 7, wherein the receiving member is a one-sided port which has a doubly stepped circular recess, the inner diameter of the first recess step being adapted to the outer diameter of one of the front end flange and the force-transmitting member, and the inner diameter of the second recess step being larger than that of the first recess step.

9. The connector of claim 7, wherein the receiving member is a one-sided port which has an axial through-bore located such that it comes to rest in opposing relation to the front end portion of the capillary conduit when the male and female assemblies are engaged with one another.

10. The connector of claim 7, wherein the receiving member is a one-sided port which has a substantially flat bottom against which a front end of the male assembly is pressed when the male and female assemblies are engaged with one another.

11. The connector of claim 1, wherein the sealing gasket is jointed radially inward to the capillary conduit via opposing inward-facing and outward-facing surfaces, respectively.

12. The connector of claim 11, wherein the joint is produced by one of adhesive, radial swaging, radial plastic deformation, and heat welding, or any combination of these techniques.

13. The connector of claim 1, wherein the force-transmitting member is not fixed to either the sealing gasket or the capillary conduit but can slide freely along an axis of the male assembly.

14. The connector of claim 1, wherein the hollow handling nut comprises a first section with an interlocking mechanism designed and configured to cooperate with a complementary interlocking mechanism foreseen at the receiving member, and further comprises a second section for manual or tool-assisted tightening the male assembly in the female assembly.

15. The connector of claim 14, wherein the complementary interlocking mechanisms comprise internal and external threads.

16. The connector of claim 14, wherein the second section comprises a polygonal feature at an outer circumference in order to assist mounting a wrench thereon.

17. The connector of claim 1, wherein a distal portion of the capillary conduit comprises an outer protective sleeve.

18. The connector of claim 1, wherein a magnitude of the said undersize is in the range of several hundred micrometers.

19. A connector for fluid chromatography having a female assembly including a receiving member being designed and configured to receive, and releasably interlock with, a male assembly, the male assembly comprising:
   a capillary conduit for transmitting chromatography fluid;
   a sealing gasket accommodating a front end portion of the capillary conduit and having a front end flange with a beveled rearward facing surface, wherein the sealing gasket stands out slightly from the front end portion of the capillary conduit in a disengaged condition of the male and female assemblies, and becomes compressed into a substantially flush alignment with the front end portion of the capillary conduit when the male and female assemblies are engaged with one another;
   a force-transmitting member slidably accommodating a portion of the sealing gasket and having a rearward facing force-receiving surface as well as a beveled front face, the dimensions of which are substantially complementary to those of the beveled rearward facing surface of the front end flange for exerting axial and radial pressurization thereon; and
   a hollow handling nut comprising a passage in which a portion of the capillary conduit is accommodated and having a forward facing force-exerting surface being configured to contact the rearward facing force-receiving surface for transmitting axial forces there-between.

20. A connector for fluid chromatography having a female assembly including a receiving member being designed and configured to receive, and releasably interlock with, a male assembly, the male assembly comprising:
   a capillary conduit for transmitting chromatography fluid;
   a sealing gasket accommodating a front end portion of the capillary conduit and having a front end flange with a beveled rearward facing surface;
   a force-transmitting member slidably accommodating a portion of the sealing gasket and having a rearward facing force-receiving surface as well as a beveled front face, the dimensions of which are substantially complementary to those of the beveled rearward facing surface of the front end flange for exerting axial and radial pressurization thereon; and
   a hollow handling nut comprising a passage in which a portion of the capillary conduit is accommodated and having a forward facing force-exerting surface being configured to contact the rearward facing force-receiving surface for transmitting axial forces there-between wherein the hollow handling nut comprises a first section with an interlocking mechanism designed and configured to cooperate with a complementary interlocking mechanism foreseen at the receiving member, and further comprises a second section for manual or tool-assisted tightening the male assembly in the female assembly, and wherein the first section comprises a cylindrical cavity in which a portion of the force-transmitting member is slidably accommodated.

* * * * *